(12) United States Patent
Liu et al.

(10) Patent No.: US 11,724,014 B2
(45) Date of Patent: Aug. 15, 2023

(54) MEMBRANE OXYGENATOR WITH BUILT-IN FILTER

(71) Applicant: JIANGSU STMED TECHNOLOGY CO., LTD., Jiangsu (CN)

(72) Inventors: Ridong Liu, Suzhou (CN); Peng Liu, Suzhou (CN); Yujie Liu, Suzhou (CN)

(73) Assignee: JIANGSU STMED TECHNOLOGY CO., LTD., Suzhou (CN)

( * ) Notice: Subject to any disclaimer, the term of this patent is extended or adjusted under 35 U.S.C. 154(b) by 0 days.

(21) Appl. No.: 18/055,826

(22) Filed: Nov. 15, 2022

(65) Prior Publication Data

US 2023/0075526 A1 Mar. 9, 2023

Related U.S. Application Data

(63) Continuation of application No. PCT/CN2021/124836, filed on Oct. 20, 2021.

(30) Foreign Application Priority Data

Jul. 14, 2021 (CN) .......................... 202110794386.8

(51) Int. Cl.
*A61M 1/16* (2006.01)
*A61M 1/36* (2006.01)

(52) U.S. Cl.
CPC ........ *A61M 1/1698* (2013.01); *A61M 1/3627* (2013.01)

(58) Field of Classification Search
CPC .... A61M 1/1563; A61M 1/16; A61M 1/1621; A61M 1/1629; A61M 1/1631; A61M 1/1698; A61M 1/3621; A61M 1/3627; A61M 1/369; A61M 2202/0413; A61M 2205/75
See application file for complete search history.

(56) References Cited

U.S. PATENT DOCUMENTS 5,270,004 A * 12/1993 Cosentino ........... A61M 1/1629
422/46
5,762,868 A * 6/1998 Leonard .............. A61M 1/3623
604/6.14

(Continued)

FOREIGN PATENT DOCUMENTS

| CN | 201643112 U | 11/2010 |
|----|-------------|---------|
| CN | 204364532 U | 6/2015 |

(Continued)

OTHER PUBLICATIONS

First Office Action in Chinese Application No. 202110794386.8 dated Dec. 3, 2021, 22 pages.

(Continued)

*Primary Examiner* — Benjamin J Klein
(74) *Attorney, Agent, or Firm* — Metis IP LLC

(57) ABSTRACT

The embodiments of the present disclosure may provide a membrane oxygenator with a built-in filter, including an upper cover, a lower cover, a shell and an oxygenation structure, wherein two ends of the shell may be respectively connected to the upper cover and the lower cover, and the oxygenation structure may be disposed in the shell, including a mandrel, a filter screen, an oxygen pressure membrane, and a temperature-changing membrane in turn from a center to an outside. The blood may flow in from an upper blood inlet of the membrane oxygenator, traverse the temperature-changing membrane, oxygen pressure membrane and filter screen in turn, and then flow out from a blood outlet under the mandrel. During a process of traversing, a flow rate of the blood may gradually slow down, and the blood may fully contact the oxygen pressure membrane and the filter screen.

11 Claims, 8 Drawing Sheets

(56) References Cited

U.S. PATENT DOCUMENTS

| | | | | | |
|---|---|---|---|---|---|
| 5,817,279 | A | * | 10/1998 | Eilers | A61M 1/1698 |
| | | | | | 422/46 |
| 5,823,987 | A | * | 10/1998 | Elgas | A61M 1/1629 |
| | | | | | 604/6.14 |
| 6,682,698 | B2 | * | 1/2004 | Chambers | A61M 1/1678 |
| | | | | | 604/6.14 |
| 8,388,566 | B2 | * | 3/2013 | Reggiani | A61M 1/322 |
| | | | | | 604/4.01 |
| 2012/0193289 | A1 | * | 8/2012 | Cloutier | A61M 1/1698 |
| | | | | | 422/46 |
| 2013/0209314 | A1 | * | 8/2013 | Roller | A61M 1/1698 |
| | | | | | 422/46 |
| 2016/0296685 | A1 | * | 10/2016 | Wu | A61M 1/1629 |
| 2020/0206404 | A1 | * | 7/2020 | Wu | A61M 1/1698 |

FOREIGN PATENT DOCUMENTS

| | | | | | |
|---|---|---|---|---|---|
| CN | 105833373 | A | | 8/2016 | |
| CN | 205849883 | U | | 1/2017 | |
| CN | 109224163 | A | | 1/2019 | |
| CN | 208893292 | U | * | 5/2019 | A61M 1/1621 |
| CN | 208893292 | U | | 5/2019 | |
| CN | 109224163 | B | * | 6/2019 | A61M 1/1623 |
| CN | 110575578 | A | | 12/2019 | |
| CN | 211024413 | U | | 7/2020 | |
| WO | WO-2021042358 | A1 | * | 3/2021 | |

OTHER PUBLICATIONS

Decision to Grant a Patent in Chinese Application No. 202110794386.8 dated Feb. 11, 2022, 4 pages.

\* cited by examiner

MEMBRANE OXYGENATOR WITH BUILT-IN FILTER

CROSS-REFERENCE TO RELATED APPLICATIONS

This application is a continuation of International Patent Application No. PCT/CN2021/124836, filed on Oct. 20, 2021, which claims priority to Chinese Patent Application No. 202110794386.8, filed on Jul. 14, 2021, the entire contents of which are incorporated herein by reference.

TECHNICAL FIELD

The present disclosure relates to the field of medical instrument, and in particular to a membrane oxygenator with a built-in filter.

BACKGROUND TECHNIQUE

A membrane oxygenator is a medical instrument that replaces lungs when a heart stops beating, which has a function of regulating a content of oxygen and carbon dioxide in the blood. It is an essential medical device for cardiovascular surgery, and it is also an essential medical device for a treatment of acute respiratory diseases and a stage of waiting for a lung transplantation. According to a principle of alveolar gas exchange, the membrane oxygenator integrates functions of oxygenation, temperature-changing, blood storage, and filtration. The working principle of the membrane oxygenator is that: venous blood in a body is drawn out of the body, and oxygen and carbon dioxide are exchanged into arterial blood after the venous blood passing through the membrane oxygenator, and then the arterial blood is returned to the human arterial system to maintain the supply of oxygenated blood for human organs and tissues, which temporarily replaces a lung function during surgery to meet the needs of patients during surgery.

A capacity of gas exchange is one of main functional indicators of a membrane oxygenator. The capacity of gas exchange generally correlates positively with an area of oxygen pressure membrane, but a larger area may cause blood damage. In addition, an oxygenator and a filter may need to be used at the same time during extracorporeal circulation. The oxygenator may be used to exchange gas in the blood to maintain the oxygen supply of the patient. The filter may be used to filter the embolus (bubbles or solid particles) in the blood. The filter may be the last safety barrier for blood returning to the body. However, the connection method between the oxygenator and the filter may increase the potential of contamination, and increase damage to the blood.

Therefore, it is desirable to provide a membrane oxygenator with a built-in filter to enhance an oxygenation effect and a filtering effect, reduce damage to blood, and reduce a risk of contamination and leakage.

SUMMARY

One or more embodiments of the present disclosure may provide a membrane oxygenator with a built-in filter. The membrane oxygenator with a built-in filter comprises an upper cover, a lower cover, a shell, and an oxygenation structure. The upper cover may be divided into a first blood path space, a first gas path space, and a first water path space in turn from a center to an outer edge. The upper cover may be provided with a gas inlet connected with the first gas path space, a first vent connected with the first blood path space, and a water inlet connected with the first water path space. The lower cover may be divided into a second blood path space, a second gas path space, and a second water path space in turn from a center to an outer edge. The lower cover may be provided with a blood outlet connected with the second blood path space, a gas outlet connected with the second gas path space, and a water outlet connected with the second water path space. Two ends of the shell may be respectively connected with the upper cover and the lower cover, and a blood inlet connected with an inner cavity of the shell may be arranged on the shell near the upper cover. The oxygenation structure may be disposed in the inner cavity of the shell. The oxygenation structure may include a mandrel, a filter screen, an oxygen pressure membrane, and a temperature-changing membrane. An upper end of the mandrel enters the first blood path space, the upper end of the mandrel may be opposite to the first vent, and a lower end of the mandrel may be opposite to the blood outlet. The filter screen may be a pleated filter screen, the filter screen may be disposed around the mandrel, and a gap may be arranged between the filter screen and the mandrel. The oxygen pressure membrane may be wrapped on an outer surface of the filter screen, and the oxygen pressure membrane may be connected with the first gas path space and the second gas path space. The temperature-changing membrane may be wrapped on an outer surface of the oxygen pressure membrane, and the temperature-changing membrane may be connected with the first water path space and the second water path space. A gap is arranged between the temperature-changing membrane and an inner wall of the shell, and a width of the gap gradually may decrease from the upper cover to the lower cover.

In some embodiments, the membrane oxygenator may further include a first plugging layer and a second plugging layer, the first plugging layer may be disposed at a junction of the shell and the upper cover, and the second plugging layer may be disposed at a junction of the shell and the lower cover. An upper end of the filter screen may be connected to the first plugging layer, and a lower end of the filter screen may be connected to the second plugging layer.

In some embodiments, the oxygen pressure membrane may include a plurality of ventilation pipes, and each ventilation pipe of the plurality of ventilation pipes may be a hollow pipe with openings at both ends. One end of each ventilation pipe may penetrate into the first plugging layer and may be connected with the first gas path space, and the other end of each ventilation pipe may penetrate into the second plugging layer and may be connected with the second gas path space. The temperature-changing membrane may include a plurality of temperature-changing pipes, and each temperature-changing pipe of the plurality of temperature-changing pipes may be a hollow pipe with openings at both ends. One end of each temperature-changing pipe may penetrate into the first plugging layer and may be connected with the first water path space, and another end of each temperature-changing pipe may penetrate into the second plugging layer and may be connected with the second water path space.

In some embodiments, the oxygenator further may include a turbulence structure for guiding blood to flow transversely, and the turbulence structure may be disposed between the shell and the temperature-changing membrane.

In some embodiments, the turbulence structure may include a plurality of protrusions protruding from the inner wall of the shell towards the temperature-changing membrane.

In some embodiments, the plurality of protrusions may be distributed in a ladder shape, and a distance between the temperature-changing membrane and the protrusion close to the upper cover may be larger than a distance between the temperature-changing membrane and the protrusion close to the lower cover.

In some embodiments, the upper cover may be further provided with a recirculation port, and the recirculation port may be connected with the first vent.

In some embodiments, the shell may be provided with a second vent.

In some embodiments, the second vent may be provided with a unidirectional breathable membrane, and the unidirectional breathable membrane may be used to intercept liquid in the shell and allow bubbles in the liquid to exit from the shell.

In some embodiments, the shell may be a cylindrical shell, and an inner diameter of the shell may decrease gradually from the upper cover to the lower cover; and a cross section of the mandrel may gradually decrease from the upper cover to the lower cover.

In some embodiments, the upper cover may be provided with a first partition ring and a second partition ring, the second partition ring may be disposed around the first partition ring, the first partition ring may partition the first blood path space and the first gas path space, and the second partition ring may partition the first gas path space and the first water path space. The lower cover may be provided with a third partition ring and a fourth partition ring, the fourth partition ring may be disposed around the third partition ring, the third partition ring may partition the second blood path space and the second gas path space, and the fourth partition ring may partition the second gas path space and the second water path space.

DESCRIPTION OF DRAWINGS

The present disclosure may be further described by way of exemplary embodiments, which may be described in detail with reference to drawings. These embodiments are not limiting, and in these embodiments, the same numbers refer to the same structures, wherein.

DETAILED DESCRIPTIONS

In order to illustrate the technical solutions of the embodiments of the present disclosure more clearly, the following briefly introduces the accompanying drawings used in the descriptions of the embodiments. Obviously, drawings described below are only some examples or embodiments of the present disclosure. Those skilled in the art, without further creative efforts, may apply the present disclosure to other similar scenarios according to these drawings. Unless obvious from the locale or otherwise specified, the same reference numbers in the figures represent the same structure or operation.

It will be understood that the terms "system," "device," "unit," "module," and/or "block" used herein are one method to distinguish different components, elements, parts, sections, or assemblies of different levels in ascending order. However, the terms may be displaced by other expressions if they may achieve the same purpose.

As shown in the present disclosure and the claims, the singular forms "a," "an," and "the" may be intended to include the plural forms as well, unless the context clearly indicates otherwise. Generally speaking, the terms "comprising" and "including" only imply that the clearly identified steps and elements are included, and these steps and elements may not constitute an exclusive list, and methods or devices may also include other steps or elements.

The flowcharts used in the present disclosure illustrate operations that systems implement according to some embodiments of the present disclosure. It should be understood that the preceding or following operations are not necessarily performed in the exact order. Instead, the various steps may be processed in reverse order or simultaneously. At the same time, one or more other operations may be added to these procedures, or one or more other operations may be removed from these procedures.

Figure 1:
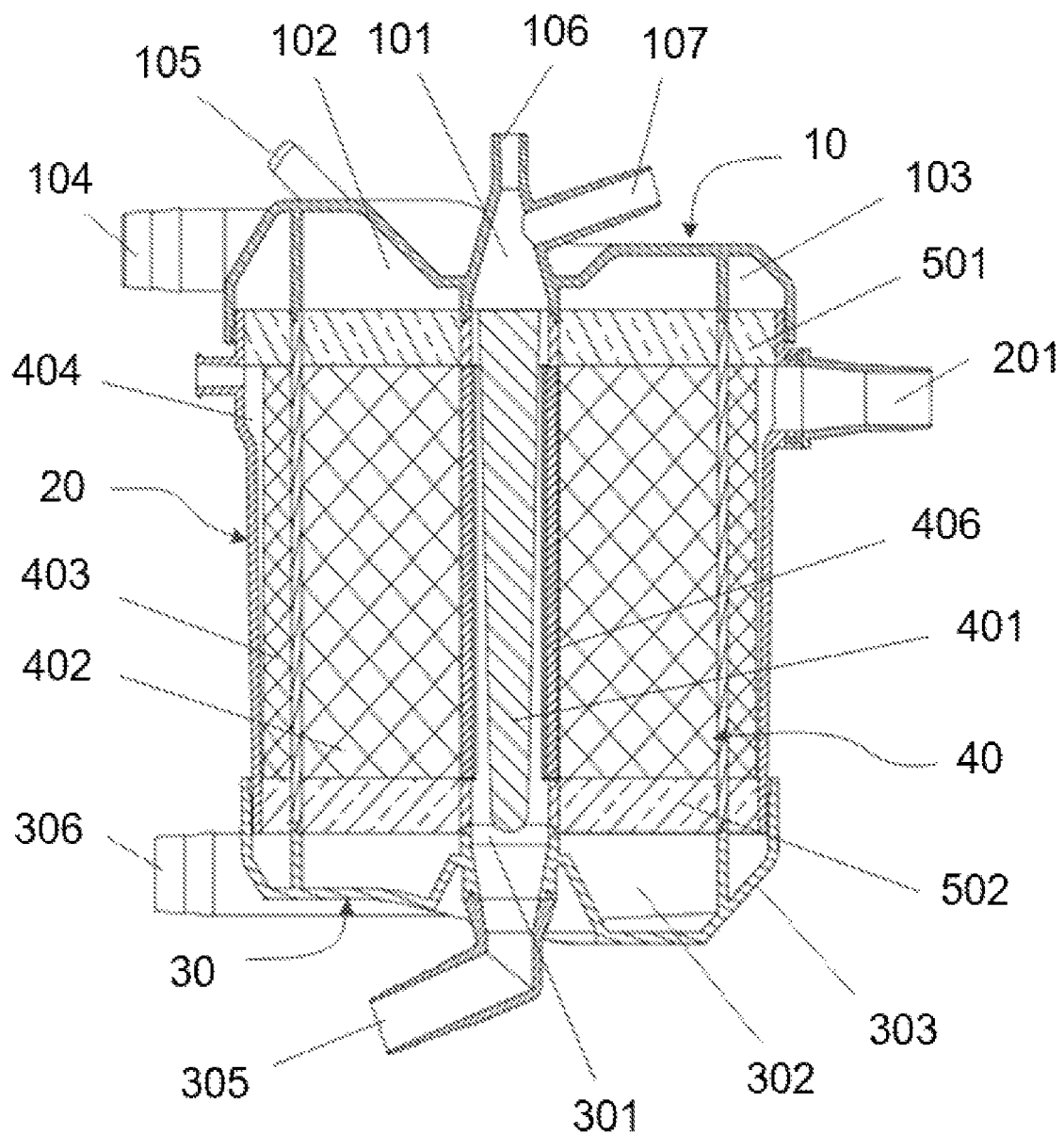
FIG. 1 is a schematic structural diagram of a membrane oxygenator with a built-in filter according to some embodiments of the present disclosure.

FIG. 1 is a schematic structural diagram of a membrane oxygenator with a built-in filter according to some embodiments of the present disclosure.

As shown in FIG. 1, the embodiments of the present disclosure may provide a membrane oxygenator 100 with a built-in filter. The membrane oxygenator 100 may include an upper cover 10, a lower cover 30, a shell 20, and an oxygenation structure 40. The ends of the shell 20 may be respectively connected with the upper cover 10 and the lower cover 30, and the oxygenation structure 40 may be disposed in the shell 20 for exchanging oxygen and carbon dioxide to convert venous blood into arterial blood. The connection method between the shell 20 and the upper cover 10 and the connection method between the shell 20 and the lower cover 30 may include but not limited to a socket connection, a snap connection, or the like.

The upper cover 10 may refer to an upper-end structure of the oxygenator. In some embodiments, the upper cover 10 may be divided into a first blood path space 101, a first gas path space 102, and a first water path space 103 in turn from a center to an outer edge. The first blood path space 101 may be a cavity for accommodating partially oxygenated blood. The first gas path space 102 may be a cavity for accommodating gas. The first water path space 103 may be a cavity for accommodating the water flowing into a temperature-changing water tank.

In some embodiments, the upper cover 10 may be provided with a gas inlet 105 connected with the first gas path space 102, a first vent 106 connected with the first blood path space 101, and a water inlet 104 connected with the first water path space 103. The gas inlet 105 may be used for an entry of oxygen in a gas source. The water inlet 104 may be used for an entry of water in the temperature-changing water tank.

The first vent 106 may be disposed opposite an upper end of mandrel 401 and may be used to discharge bubbles in the blood. In some embodiments, when gathering near the mandrel 401 along the blood flow, the gas in the membrane oxygenator may be easier to be discharged through the first vent 106 on the top of the upper cover 10 due to the upward movement of bubbles in the blood. For the specific content of the mandrel, please refer to the related descriptions below.

In some embodiments, the upper cover 10 may also be made of a transparent material to intuitively observe whether there are residual bubbles inside the oxygenator, and determine whether there is a safety risk in a product or an overall circuit by observing an aggregate situation of bubbles at the top of the upper cover, which may be convenient to take measures at the first time to avoid serious consequences.

In some embodiments, the upper cover 10 may be further provided with a recirculation port 107, and the recirculation port 107 may be connected with the first vent 106.

The recirculation port 107 may be a channel for eliciting oxygenated blood. In some embodiments, the oxygenated blood may be drawn from the vicinity of the mandrel 401 by connecting the recirculation port 107 when it is necessary to additionally elicit the oxygenated blood for other uses. The connection method for connecting the recirculation port 107 may be a socket connection, a screw connection, or the like.

In some embodiments, the upper cover 10 may further include an upper cover body, a first partition ring (not shown in the figure), and a second partition ring (not shown in the figure).

The upper cover body may refer to a main structure of the upper cover 10. In some embodiments, the upper cover body may be provided with an opening and a bottom opposite to the opening, and the bottom may protrude away from the opening, so that a middle portion of the upper cover body may be concave.

The first partition ring may be used to partition the first blood path space 101 and the first gas path space 102. In some embodiments, the first partition ring may be disposed in the upper cover body, and the first partition ring may divide a concave space on the upper cover body into two spaces including an inner space and an outer space, and a space inside the first partition ring may be the first blood path space 101.

The second partition ring may be used to partition the first gas path space 102 and the first water path space 103. In some embodiments, the second partition ring may be disposed around the first partition ring and may divide a space outside the first partition ring into two spaces including an inner space and an outer space, a space located between the first partition ring and the second partition ring may be the first gas path space 102, and a space located between the second partition ring and an edge of the upper cover body may be the first water path space 103.

In some embodiments, the gas inlet 105 and the water inlet 104 may both be disposed on the upper cover body, the gas inlet 105 may be located between the first partition ring and the second partition ring, and the water inlet 104 may be located between the second partition ring and the edge of the upper cove body.

The lower cover may refer to a lower-end structure of the oxygenator. In some embodiments, the lower cover 30 may be divided into a second blood path space 301, a second gas path space 302, and a second water path space 303 in turn from a center to an outer edge. The second blood path space 301 may be different from the first blood path space 101, and may also refer to a cavity for accommodating oxygenated blood (i.e., arterial blood). The second gas path space 302 may refer to a cavity for accommodating carbon dioxide gas. The second water path space 303 may refer to a space for accommodating water input by a temperature-changing pipe.

In some embodiments, the lower cover 30 may be provided with a blood outlet 305 connected with the second blood path space 301, a gas outlet (not shown in the figure) connected with the second gas path space 302, and a water outlet 306 connected with the second water path space 303.

The blood outlet 305 may be used for an outflow of oxygenated blood (i.e., arterial blood). In some embodiments, the blood outlet may be located at a bottom of a center of the oxygenator, which may enable doctors to recover residual blood as much as possible after surgery, reduce a risk of cross-infection caused by allogeneic blood transfusion, and also reduce use of stock blood.

The gas outlet may be used to remove carbon dioxide in the blood. The water outlet 306 may be used to return the water in the temperature-changing pipe to the temperature-changing water tank.

In some embodiments, the lower cover 30 may further include a lower cover body, a third partition ring (not shown in the figure), and a fourth partition ring (not shown in the figure).

The lower cover body may refer to a main structure of the lower cover 30. In some embodiments, the lower cover body may be provided with an opening and a bottom opposite to the opening, and the bottom may protrude away from the opening, so that a middle of the lower cover body may be concave.

The third partition ring may be used to partition the second blood path space 301 and the second gas path space 302. In some embodiments, the third partition ring may be disposed in the lower cover body, and may divide a concave space on the lower cover body into two spaces including an inner space and an outer space, and a space inside the third partition ring may be the second blood path space 301.

The fourth partition ring may be used to partition the second gas path space 302 and the second water path space 303. In some embodiments, the fourth partition ring may be disposed around the third partition ring, and the fourth partition ring may divide a space outside the third partition ring into two spaces including an inner space and an outer space, a space located between the third partition ring and the fourth partition ring may be the second gas path space 302, and a space located between the fourth partition ring and an edge of the lower cover body may be the second water path space 303.

In some embodiments, the blood outlet 305, the gas outlet, and the water outlet 306 may all be disposed on the upper cover body, and the blood outlet 305 may be located within the third partition ring, the gas outlet may be located between the third partition ring and the fourth partition ring, and the water outlet 306 may be located between the fourth partition ring and the edge of the upper cover body.

The shell 20 may be used to carry main components of the oxygenator. In some embodiments, two ends of the shell 20 may be respectively connected with the upper cover 10 and the lower cover 30, and a blood inlet 201 connected with an inner cavity of the shell may be arranged on the shell 20 near the upper cover 10.

In some embodiments, the shell 20 may be cylindrical, a first shell partition and a second shell partition may be arranged inside the shell 20, and the first shell partition and the second shell partition may be annular parts, two ends of the first shell partition may be respectively connected with the first partition ring of the upper cover 10 and the third partition ring of the lower cover 30, and two ends of the second shell partition may be respectively connected with the second partition ring of the upper cover 10 and the fourth partition ring of the lower cover 30. The connection method between the first shell partition and the first partition ring, between the first shell partition and the third partition ring, between the second shell partition and the second partition ring, between the second shell partition and the fourth partition ring may be a welding, a socket connection, or the like.

In some embodiments, the shell 20 may be further provided with a second vent 202. The function of the second vent 202 may be the same as that of the first vent 106 and may be used to discharge bubbles in the blood. For more information about the second vent, please refer to FIG. 5 and its related descriptions thereof.

The oxygenation structure 40 may be a main structure of the oxygenator for exchanging oxygen and carbon dioxide to convert venous blood into arterial blood. In some embodiments, the oxygenation structure 40 may be disposed inside the shell 20 and may include a mandrel 401, a filter screen 406, an oxygen pressure membrane 402, and a temperature-changing membrane 403. Specifically, the mandrel 401 may be disposed in the first shell partition, the filter screen 406 may be disposed on the first shell partition, the oxygen pressure membrane 402 may be disposed between the first shell partition and the second shell partition, and the temperature-changing membrane 403 may be disposed between an inner wall of the shell 20 and the second shell partition.

The mandrel 401 may be used to converge and guide oxygenated blood (i.e., arterial blood) into the second blood path space 301. In some embodiments, an upper end of the mandrel 401 may enter the first blood path space 101, and a lower end of the mandrel 401 may be opposite to the blood outlet 305.

The structure of the mandrel 401 may not be limited and may be a cylindrical structure, a pyramid structure, or the like. In some embodiments, the mandrel 401 may be set as a pyramid structure, so that a cross section of the mandrel 401 may gradually decrease from the upper cover 10 to the lower cover 30, so as to better gather the oxygenated blood.

The filter 406 may be used to filter the oxygenated blood. The structural shape of the filter 406 may not be limited, and may be any other shape, such as a rectangle. In some embodiments, the filter screen 406 may be a pleated filter screen.

In some embodiments, the filter screen may be disposed around the mandrel 401, a gap may be arranged between the filter screen 406 and the mandrel 401, and the blood may converge to a lower part of the mandrel 401 along the gap. For more information about the filter screen 406, please refer to FIG. 4 and its related descriptions thereof.

The oxygen pressure membrane 402 may be a structure for exchanging oxygen and carbon dioxide. In some embodiments, the oxygen pressure membrane 402 may be wrapped on an outer surface of the filter screen 406, and the oxygen pressure membrane 402 may be connected with the first gas path space 102 and the second gas path space 302.

In some embodiments, the oxygen pressure membrane 402 may include a plurality of ventilation pipes (not shown in the figure).

The ventilation pipes may be pipes for gas exchange with the blood. In some embodiments, each ventilation pipe of the plurality of ventilation pipes may be a hollow pipe with openings at both ends, and the aperture size of each ventilation pipe may be within a range of 0.1 um-5 um. One end of each ventilation pipe may penetrate into the first plugging layer 501 and may be connected with the first gas path space 102, and the other end of each ventilation pipe may penetrate into the second plugging layer 502 and may be connected with the second gas path space 302. Pipe walls of at least part of the plurality of ventilation pipes may be provided with micropores, and the micropores may only allow gas to pass through and plug blood cells from passing through. In fact, the pipe wall of the ventilation pipe may also be regarded as a semipermeable membrane that may only allow gas to pass through. The membrane oxygenator may realize a gas exchange process in the blood through the semipermeable membrane.

For specific contents of the first plugging layer 501 and the second plugging layer 502, reference may be made to the related descriptions below.

The temperature-changing membrane 403 may be used for heat exchange with blood to control blood temperature. In some embodiments, the temperature-changing membrane 403 may be wrapped on an outer surface of the oxygen pressure membrane 402, and the temperature-changing membrane 403 may be connected with the first water path space 103 and the second water path space 303. A gap 404 may be arranged between the temperature-changing membrane 403 and the shell 20, and a width of the gap 404 may gradually decrease from the upper cover 10 to the lower cover 30. For more information about the gap 404, please refer to FIG. 2 and its related descriptions thereof.

In some embodiments, the temperature-changing membrane 403 may include a plurality of temperature-changing pipes (not shown in the figure).

The plurality of temperature-changing pipes may be pipes for heat exchange with the blood. In some embodiments, each temperature-changing pipe of the plurality of temperature-changing pipes may be a hollow pipe with openings at both ends, one end of each temperature-changing pipe may penetrate the first plugging layer 501 and may be connected with the first water path space 103, and the other end of each temperature-changing pipe may penetrate the second plugging layer 502 and may be connected with the second water path space 303.

In some embodiments, both the oxygen pressure membrane 402 and the temperature-changing membrane 403 may be composed of a large number of thin-walled hollow pipes. The difference may be that at least part of the hollow pipes used in the oxygen pressure membrane 402 may be porous membranes for gas exchange with the blood, and all the hollow pipes used in the temperature-changing membrane 403 may be non-porous membranes for flow conduction and heat exchange with the blood outside the hollow pipes.

In some embodiments, the membrane oxygenator 100 may also include a flow turbulence structure for guiding blood to flow transversely.

In some embodiments, the turbulence structure may be disposed between the shell 20 and the temperature-changing membrane 403. For more content of the turbulence structure, please refer to FIG. 3 and its related descriptions thereof.

In some embodiments, the membrane oxygenator 100 may further include a first plugging layer 501 and a second plugging layer 502, the first plugging layer 501 may be disposed at a junction of the shell 20 and the upper cover 10, and the second plugging layer 502 may be disposed at a junction of the shell 20 and the lower cover 30.

The first plugging layer 501 may be used for isolating the inner cavity of the shell 20 from each space of the upper cover 10. In some embodiments, the first plugging layer 501 may isolate the first blood path space 101, the first gas path space 102, and the first water path space 103, and may also isolate the inner cavity of the shell 20 from each space of the upper cover 10.

The second plugging layer 502 may be used to isolate the inner cavity of the shell 20 from each space of the lower cover 30. In some embodiments, the second plugging layer 502 may isolate the second blood path space 301, the second gas path space 302, and the second water path space 303, and may also isolate the inner cavity of the shell 20 from each space of the lower cover 30.

In some embodiments, the upper end of the filter screen 406 may be connected with the first plugging layer 501, and the lower end of the filter screen 406 may be connected with the second plugging layer 502. The connection method may include but not limited to a bonding, or the like.

A membrane oxygenator may be a medical device that may replace human lung function for extracorporeal gas exchange during surgery or life support. The use method and working process of the membrane oxygenator 100 provided by some embodiments of the present disclosure may be as follows.

During surgery or maintenance of vital signs, blood inlet 201 may be connected with a human vein through a hose, blood outlet 305 may be connected with a human artery through a hose, water inlet 104 and water outlet 306 may be respectively connected with a temperature-changing water tank through hoses, and gas inlet 105 may be connected with a gas source through a hose. Water with a set temperature may be inputted into an inner cavity of each temperature-changing pipe composing the temperature-changing membrane 403 through the water inlet 104 by the temperature-changing water tank, and oxygen with a set concentration may be inputted into an inner cavity of each ventilation pipe composing the oxygenation membrane through the gas inlet 105 by the gas source. When venous blood enters the shell 20 through the blood inlet 201, the blood flowing through the temperature-changing membrane 403 may perform a heat exchange with the blood through an outer wall of the temperature-changing pipe, so as to achieve a purpose of heating or cooling the blood. The venous blood that has completed the heat exchange may enter the oxygen pressure membrane 402 transversely, the gas may be arranged inside the ventilation pipe, and the blood may be arranged outside the ventilation pipe. The gas and blood may exchange oxygen and carbon dioxide through a diffusion on both sides of the semipermeable membrane. The carbon dioxide in the venous blood may enter the inner cavity of the ventilation pipe, the oxygen in the ventilation pipe may enter the blood, and then a process of converting venous blood into arterial blood may be completed. Further, the arterial blood may reach the mandrel 401 through the filter screen 406, flow into the second blood path space 301 along the mandrel 401, and then be returned to the human body from the blood outlet 305 to maintain the oxygen supply of the patient.

The capacity of gas exchange may be not only related to the surface area of the oxygen pressure membrane and the oxygen concentration of the gas source, but also have a direct relationship with a setting of a blood flow route. A large number of experiments have shown that no matter whether the gas route and the blood flow route are in the opposite or the same direction, the longer the route is, the worse the capacity of gas exchange may be, and the capacity of gas exchange may approach 0 when the route reaches 2 meters. Therefore, the higher the proportion of the blood flow route traversing the oxygen pressure membrane is, the better the oxygenator effect may be.

In some embodiments, the membrane oxygenator with a built-in filter has an arrangement of the blood inlet and the blood outlet, the gap between the temperature-changing membrane and the inner wall of the shell, and the turbulent structure, thereby increasing the ratio of blood traversing the oxygen pressure membrane, improving the oxygenation effect of the membrane oxygenator and achieving the same capacity of gas exchange by using an oxygen pressure membrane with a smaller area. Moreover, through the above design, the membrane oxygenator may have a larger blood flow buffer area. When the blood enters the oxygenator, more blood may traverse the temperature-changing membrane and the oxygen pressure membrane at a slower speed. The contact time between the blood and the temperature-changing membrane and the contact time between the blood and the oxygen pressure membrane may be longer, which can obtain a better temperature-changing efficiency and a better oxygenation effect, and can also make the oxygenator resistance loss smaller, reducing damage to the blood caused by the resistance.

Figure 2:
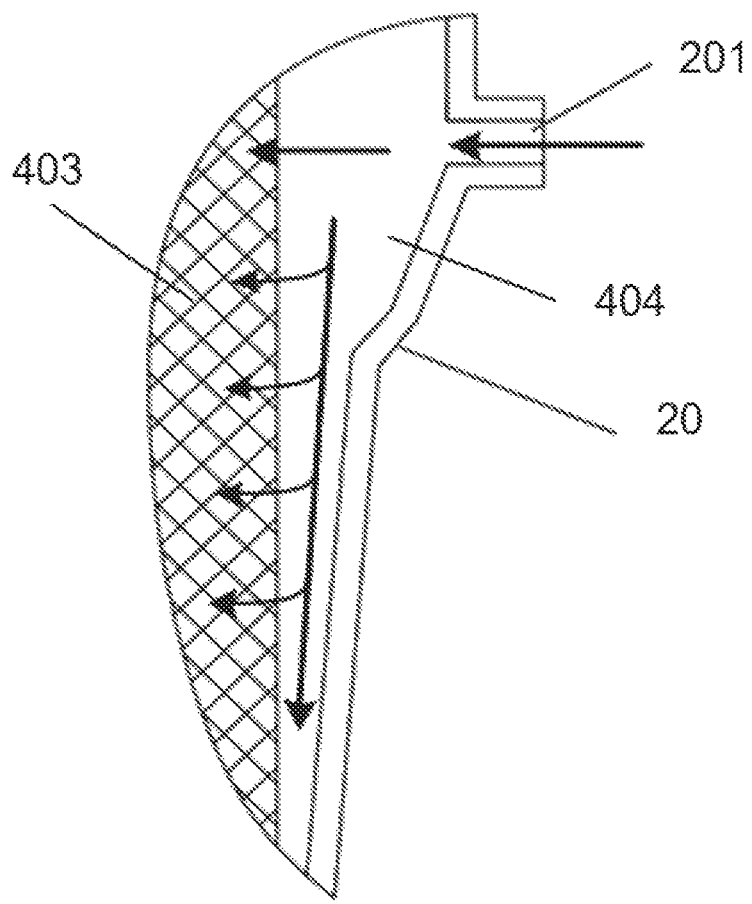
FIG. 2 is a partial schematic diagram of a structure of a shell according to some embodiments of the present disclosure.

FIG. 2 is a partial schematic diagram of a structure of a shell according to some embodiments of the present disclosure.

As shown in FIG. 2, a gap 404 may be arranged between the temperature-changing membrane 403 and the inner wall of the shell 20, the width of the gap 404 may gradually decrease from the upper cover 10 to the lower cover 30, and the blood inlet 201 may be close to the upper cover 10. When blood enters the membrane oxygenator 100 from the blood inlet 201, the gap 404 between the temperature-changing membrane 403 and the inner wall of the shell 20 may be first filled. Since the gap 404 is wide at the top and narrow at the bottom, a small amount of blood may fill a lower part of the gap 404, and more blood may reside in an upper part of the gap 404. Driven by continuous blood injected from the blood inlet 201, the blood residing in the upper part of the gap 404 may continue to transversely pass through the temperature-changing membrane 403 and the oxygen pressure membrane 402, then may enter the space where the mandrel 401 is located, and then may be returned to the human body through the blood outlet 305 connected with the space. The upper cover 10, the lower cover 30, the mandrel 401, and the oxygen pressure membrane 402 may refer to FIG. 1 and its related descriptions thereof.

In some embodiments, in order to make the gap 404 between the temperature-changing membrane 403 and the shell 20 gradually decrease, any one of the following methods or a combination thereof may be used.

(1) The shell 20 may be designed as a column so that an inner diameter of the shell 20 may decrease gradually from the upper cover 10 to the lower cover 30.

(2) The temperature-changing pipes may be arranged and designed so that the end of the temperature-changing membrane 403 close to the lower cover 30 may be closer to the inner wall of the shell 20 than the end of the temperature-changing membrane 403 close to the upper cover 10.

In some embodiments, the gap 404 between the temperature-changing membrane 403 and the shell 20 decreasing gradually may be realized in any other possible method.

In some embodiments of the present disclosure, by adopting a design in which the gap between the temperature-changing membrane and the shell gradually decreases, the blood in the upper part of the gap may continue to transversely pass through the temperature-changing membrane and the oxygen pressure membrane, which can better ensure the oxygenation effect of the membrane oxygenator.

Figure 3:
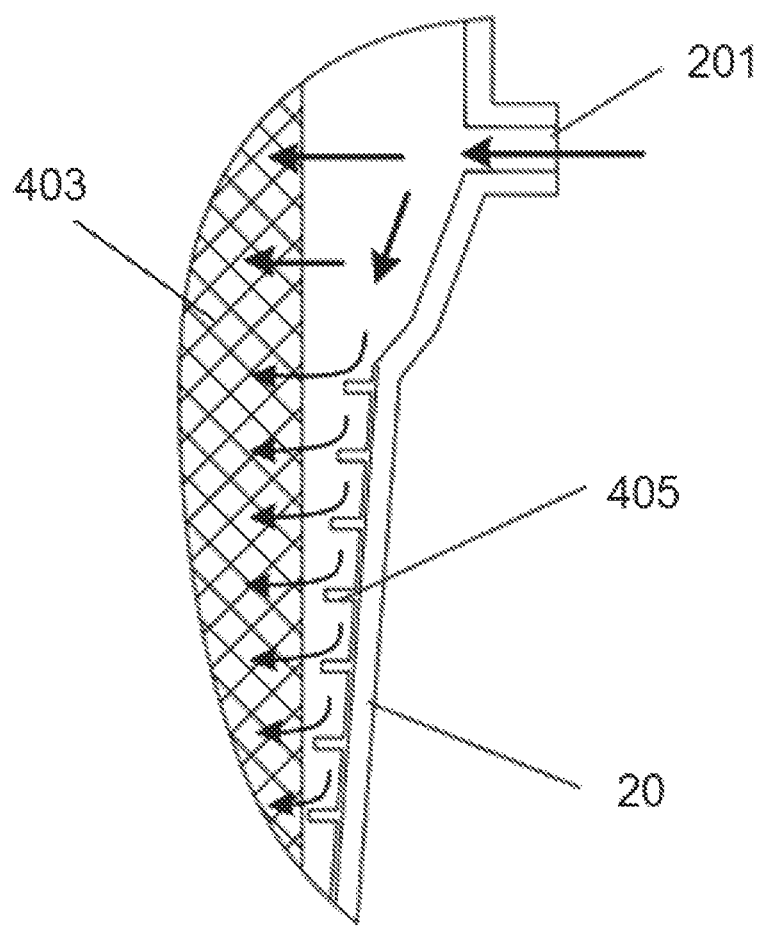
FIG. 3 is a partial schematic diagram of another structure of the shell according to some embodiments of the present disclosure.

FIG. 3 is a partial schematic diagram of another structure of the shell according to some embodiments of the present disclosure.

As shown in FIG. 3, the turbulence structure may include a plurality of protrusions 405 protruding from the inner wall of the shell 20 towards the temperature-changing membrane 403. In some embodiments, the blood may enter the gap between the inner wall of the shell 20 and the temperature-changing membrane 403 from the blood inlet 201 and may be plugged by the protrusions 405 during flowing to the lower cover 30, which may force the blood flow to change the flow direction to enter the temperature-changing membrane 403 transversely.

In some embodiments, the plurality of protrusions 405 constituting the turbulence structure may be distributed in a ladder shape and a distance between the temperature-changing membrane 403 and the protrusion 405 close to the upper cover 10 may be larger than a distance between the temperature-changing membrane 403 and the protrusion 405 close to the lower cover 30. By adopting this design, the blood flowing to the lower cover 30 may be plugged by each of the protrusions 405, so that as much blood as possible may traverse the temperature-changing membrane 403 and the oxygen pressure membrane 402 for sufficient heat exchange and gas exchange.

In some embodiments of the present disclosure, by designing the turbulent structure and distributing the plurality of protrusions constituting the turbulent structure in a ladder shape, the blood may better traverse the temperature-changing membrane and the oxygen pressure membrane for sufficient heat exchange and gas exchange, which is beneficial to improve the oxygenation effect of the membrane oxygenator.

Figure 4:
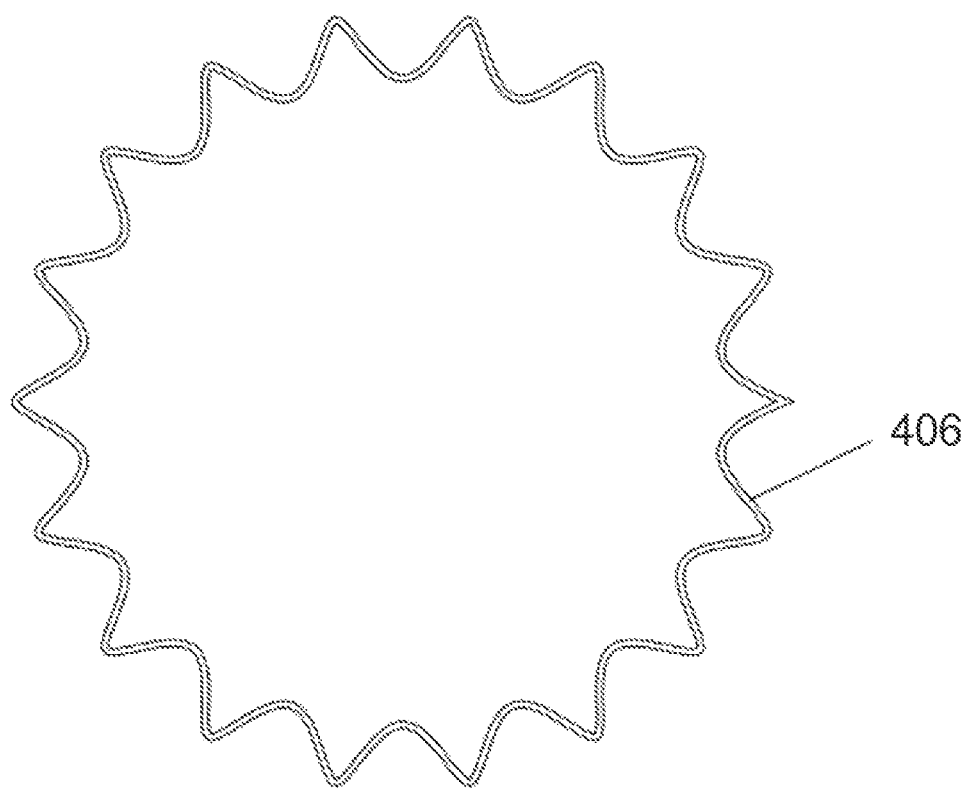
FIG. 4 is a schematic diagram of a structure of a filter screen according to some embodiments of the present disclosure.

FIG. 4 is a schematic diagram of a structure of a filter screen according to some embodiments of the present disclosure.

In some embodiments, the filter screen 406 may be a pleated filter screen. As shown in FIG. 4, the pleated filter screen may include a plurality of pairs of opposite sides of pleats, the plurality of oppositely facing pleats may be provided with outer pleat tips, outer pleat valleys, inner pleat tips, and inner pleat valleys. The opposite side of the outer pleat tips may be the inner pleat valleys, and the opposite side of the outer pleat valleys may be the inner pleat tips.

In some embodiments, the filter screen 406 may form a closed-loop structure around the mandrel 401, and its outer pleat tips and outer pleat valleys may face the oxygen pressure membrane 402, and its inner pleat tips and inner pleat valleys may face the mandrel 401.

In some embodiments of the present disclosure, by utilizing the feature that the pleated filter screen occupies a small space but has a large expansion area, the contact area between the blood and the filter screen may be increased, which may be beneficial to improve the filtering effect of the membrane oxygenator.

Figure 5:
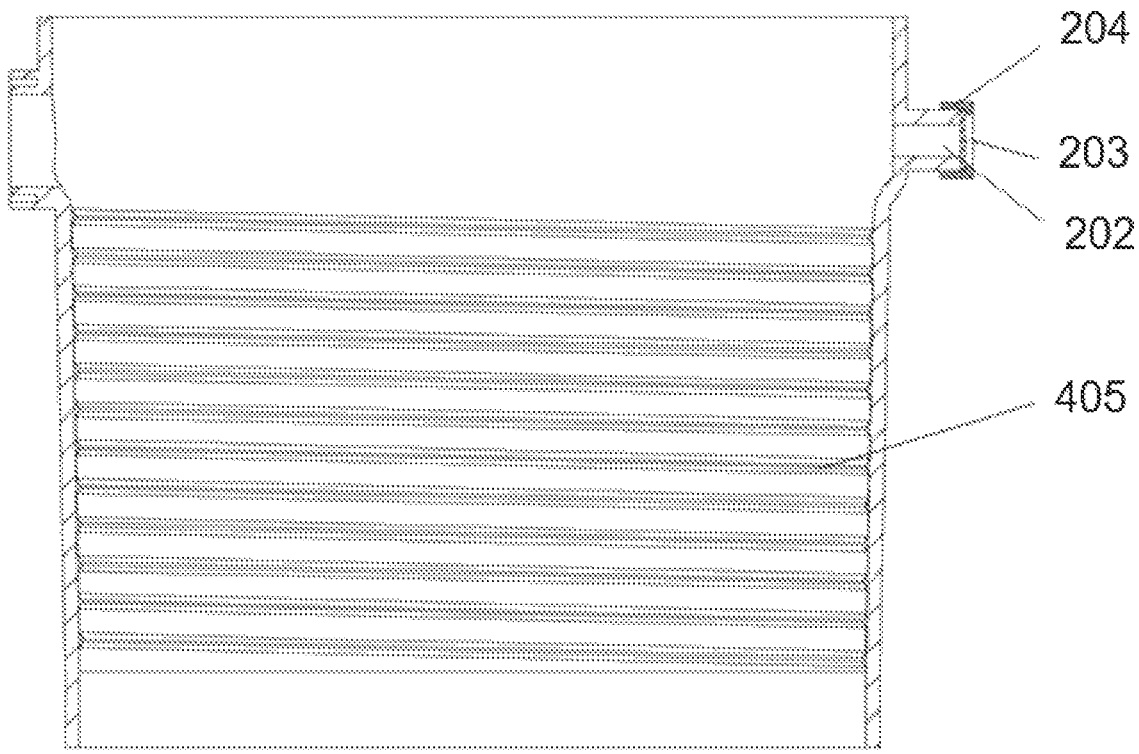
FIG. 5 is a schematic diagram of a structure of a shell provided with a second vent according to some embodiments of the present disclosure.

FIG. 5 is a schematic diagram of a structure of a shell provided with a second vent according to some embodiments of the present disclosure.

In some embodiments, since the shell 20 may be in the form of a cylinder, some bubbles may not enter the vicinity of the mandrel 401, but accumulate on the upper part of the shell 20. In order to remove this part of the bubbles, a second vent 202 (as shown in FIG. 5) may be disposed on the shell 20 near the upper cover 10.

In some embodiments, a hose may be used to connect with the second vent 202 with other components for venting.

In some embodiments, a unidirectional breathable membrane 203 may also be disposed on the second vent 202, and the unidirectional breathable membrane 203 may be used to intercept liquid in the shell 20 and allow bubbles in the liquid to exit from the shell 20. Specifically, as shown in FIG. 5, a compression cover 204 may be sheathed on the unidirectional breathable membrane and the compression cover 204 may be connected with the second vent 202 by a method such as a thread or a snap, so as to compress and fix the unidirectional breathable membrane 203. The unidirectional breathable membrane 203 may be provided with micropores, which may only allow gas but not blood to pass through. Therefore, the second vent 202 provided with the unidirectional breathable membrane 203 may achieve a function of blood interception and discharging bubbles in the blood with no need to be connected with other components.

In some embodiments of the present disclosure, a second vent may be used to discharge the bubbles accumulated in the upper part of the shell, and a vent function can be better realized and a capability of discharging bubbles of the membrane oxygenator can be enhanced by matching the first vent.

Figure 6:
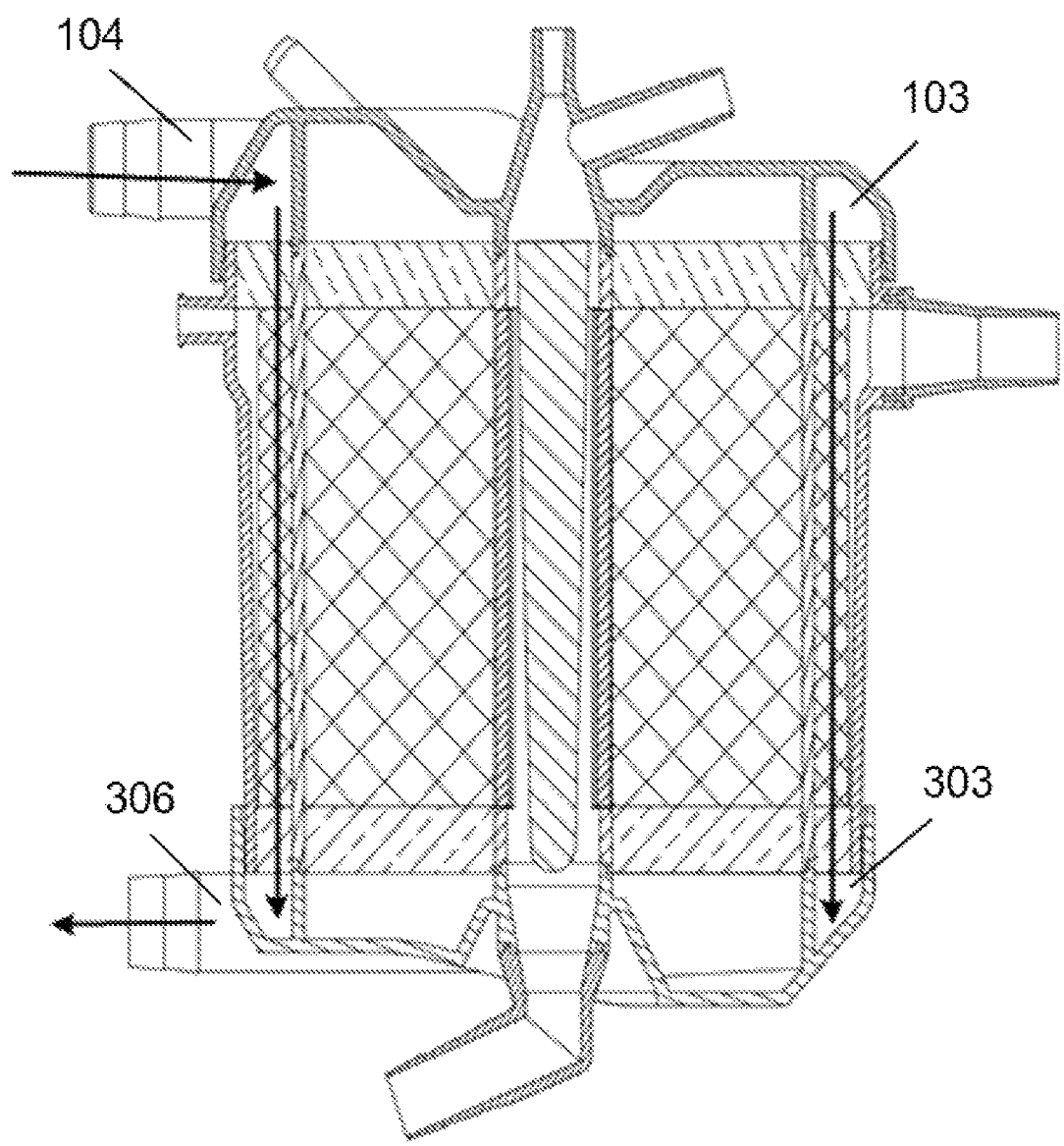
FIG. 6 is a schematic diagram of a water flow direction in the membrane oxygenator according to some embodiments of the present disclosure.

FIG. 6 is a schematic diagram of a water flow direction in the membrane oxygenator according to some embodiments of the present disclosure.

As shown in FIG. 6, in some embodiments, the water flow direction in the membrane oxygenator may be as follows. The water in the temperature-changing water tank may flow into the first water path space 103 from the water inlet 104, and enter the second water path space 303 through the temperature-changing pipes, then flow back to the temperature-changing water tank from the water outlet 306. When the blood flows through the temperature-changing pipes, a heat exchange may be performed between the blood and the water in the temperature-changing pipes to adjust the blood temperature to a required temperature range.

Figure 7:
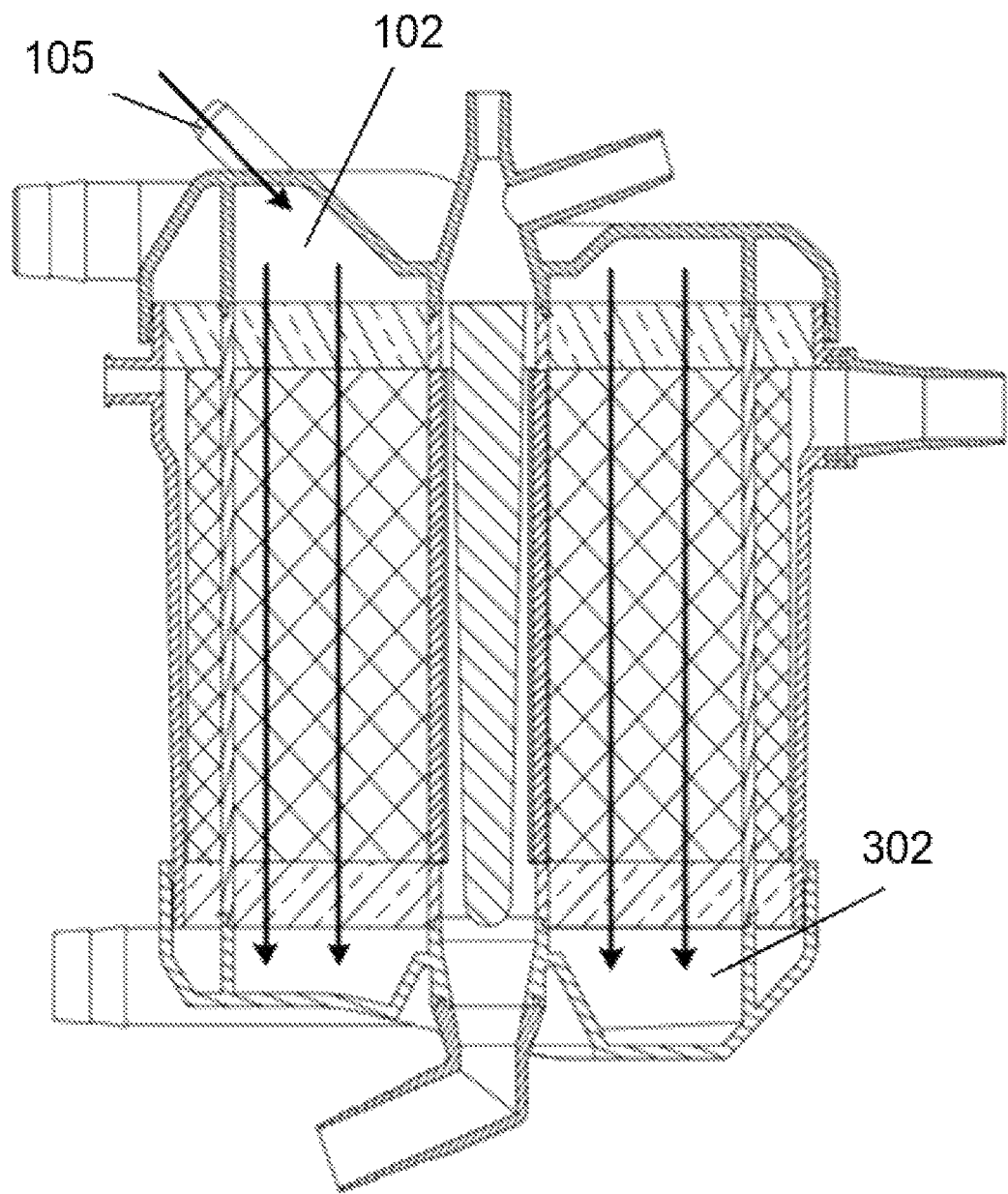
FIG. 7 is a schematic diagram of a gas flow direction in the membrane oxygenator according to some embodiments of the present disclosure.

FIG. 7 is a schematic diagram of a gas flow direction in the membrane oxygenator according to some embodiments of the present disclosure.

As shown in FIG. 7, in some embodiments, the gas flow direction in the membrane oxygenator may be as follows. The oxygen in the gas source may enter the first gas path space 102 from the gas inlet 105, then flow into the ventilation pipes, and perform a gas exchange with the ventilation pipes based on the blood in the ventilation pipes. The oxygen in the ventilation pipes may be combined with the blood, and the carbon dioxide in the blood may enter the ventilation pipes, then flow into the second gas path space 302, and may be discharged from the gas outlet.

Figure 8:
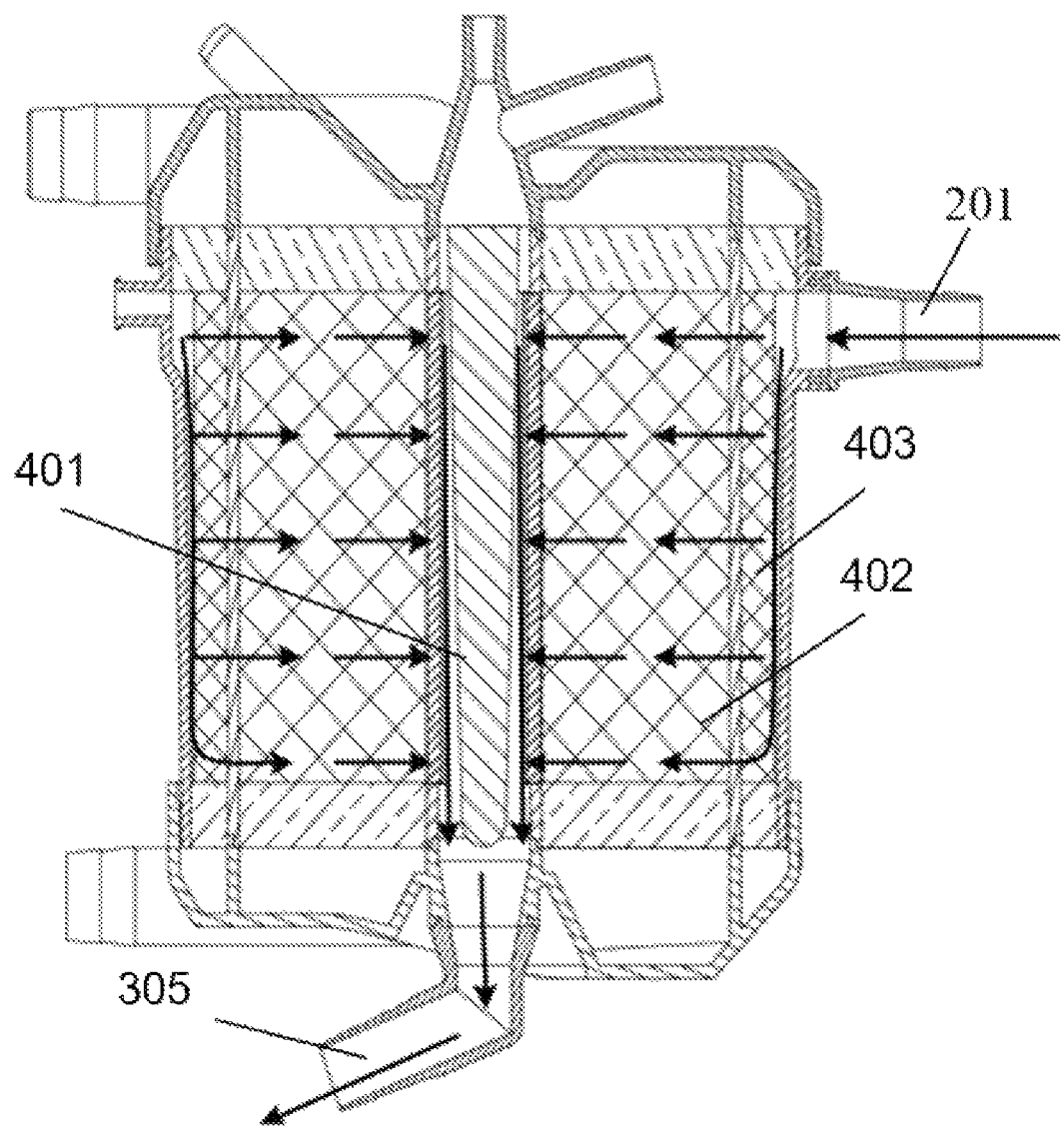
FIG. 8 is a schematic diagram of a blood flow direction in the membrane oxygenator according to some embodiments of the present disclosure.

FIG. 8 is a schematic diagram of a blood flow direction in the membrane oxygenator according to some embodiments of the present disclosure.

As shown in FIG. 8, in some embodiments, the blood flow direction in the membrane oxygenator may be as follows. The blood may enter the membrane oxygenator from the blood inlet 201, traverse the temperature-changing membrane 403 and the oxygen pressure membrane 402, then converge in a space where the mandrel 401 is located, and flow out along the blood outlet 305.

The membrane oxygenator provided by some embodiments of the present disclosure may have the following advantages.

(1) Improving the oxygenation effect. Since the blood passes through the temperature-changing membrane, the oxygen pressure membrane and the filter screen transversely, the flow rate of the blood may gradually slow down during this process, and the contact time with the oxygen pressure membrane may become longer, so the oxygenation effect of the membrane oxygenator can be improved.

(2) Improving the filtering effect. The influencing factors of the filtering effect may include area and speed (that is, a mixing contact time of the fluid and the membrane may have a greater impact on the filtering effect, and the longer the mixing contact time is, the better the filtering effect may be), the lower the flow rate is, the better the interception effect may be, and the better the filtering effect may be. In some embodiments of the present disclosure, since the blood transversely passes through the temperature-changing membrane, the oxygen pressure membrane, and the filter screen, the flow rate of the blood may gradually slow down during this process. When the blood reaches the filter screen, the flow rate of the blood may further decrease. The contact time between the filter screen and the blood may increase, which can intercept impurities and bubbles in the blood to obtain a better filtering effect. In addition, a pleated filter screen may have a larger surface area, which can increase the contact area between the blood and the filter screen, which can further improve the filtering effect.

(3) Reducing damage to the blood. The membrane oxygenator provided by some embodiments of the present disclosure may include a mandrel, a filter screen, an oxygen pressure membrane, and a temperature-changing membrane in order from a center to outside. The blood flow direction may be from an upper side to a bottom side. The blood may stay in the upper part of the oxygenator for a long time, and the proportion of traversing the temperature-changing membrane, the oxygen pressure membrane, and the filter screen may be large. During a traversing process, the blood flow rate may gradually slow down, so that the blood may fully contact the oxygen pressure membrane and the filter screen at a low flow rate, and it is not need to increase pressure to drive blood flow, thus reducing the damage to the blood.

The basic concepts have been described above. Obviously, for those skilled in the art, the above detailed disclosure is merely an example and does not constitute a limitation of the present disclosure. Although not explicitly described herein, various modifications, improvements, and corrections to the present disclosure may be performed by those skilled in the art. Such modifications, improvements, and corrections may be suggested in the present disclosure, so such modifications, improvements, and corrections may still belong to the spirit and scope of the exemplary embodiments of the present disclosure.

Meanwhile, the present disclosure may use specific words to describe the embodiments of the present disclosure. For example, "one embodiment," "an embodiment," and/or "some embodiments" may mean a certain feature, structure, or characteristic associated with at least one embodiment of the present disclosure. Therefore, it should be emphasized and noted that two or more references to "an embodiment" or "one embodiment" or "an alternative embodiment" in different places in the present disclosure may be not necessarily referred to the same embodiment. Furthermore, certain features, structures, or characteristics of the one or more embodiments of the present disclosure may be combined as appropriate.

Furthermore, unless explicitly stated in the claims, the order of processing elements and sequences described in the present disclosure, the use of alpha and number, or the use of other names may be not intended to limit the order of the processes and methods of the present disclosure. While the preceding disclosure discusses some embodiments of the invention that are presently believed to be helpful, it is to be understood that such details may be only for purposes of illustration and that the appended claims may be not limited to the disclosed embodiments. On the contrary, the claims may be intended to cover all modifications and equivalent combinations that come within the spirit and scope of the embodiments of the present disclosure. For example, although the system components described above may be implemented by hardware devices, they may also be implemented by software-only solutions, such as installing the described systems on existing servers or mobile devices.

Similarly, it should be noted that, in order to simplify the expressions disclosed in the present disclosure and thereby help the understanding of one or more embodiments of the invention, in the preceding descriptions of the embodiments of the present disclosure, various features may sometimes be combined into one embodiment, in one drawing or descriptions thereof. However, this method for disclosure may not imply that an object of the present disclosure requires more features than are recited in the claims. Indeed, there are fewer features of an embodiment than all of the features of a single embodiment disclosed above.

In some embodiments, numbers representing quantities/properties used to describe and claim certain embodiments of the present disclosure may be understood as modified by the terms "about", "approximately" or "substantially" in some cases. Unless stated otherwise, "about", "approximately" or "substantially" may mean that a variation of ±20% may be allowed for the stated number. Accordingly, in some embodiments, numerical parameters used in the present disclosure and claims may be approximate values, which may be changed according to the features required by individual embodiments. In some embodiments, the numerical parameters may consider specified significant digits and adopt a method for general digit reservation. Although the numerical fields and parameters used to confirm a range breadth in some embodiments of the present disclosure may be approximate values, in specific embodiments, such values may be set as accurately as possible within a feasible range.

Each patent, patent application, patent application publication, or other materials (such as articles, books, specifications, publications, documents, events, and/or similar things) cited in the present disclosure may be hereby incorporated into the present disclosure as a reference. Any indictment documentation relating to the aforementioned documents, any such document inconsistent with or conflicting with the present disclosure, or any such document limiting the broad scope of the claims to which the present disclosure relates sooner or later may be also excluded. For example, if there is any inconsistency or conflict between the descriptions, definition, and/or use of terms in the auxiliary materials of the present disclosure and the content of the present disclosure, the descriptions, definition, and/or use of terms in the present disclosure may be subject to the present disclosure.

Finally, it should be understood that the embodiments described in the present disclosure may only be used to illustrate principles of the embodiments of the present disclosure. Other variations may also belong to the scope of the present disclosure. Therefore, as an example and not a limitation, alternative configurations of the embodiments of the present disclosure may be regarded as consistent with the teaching of the present disclosure. Accordingly, the embodiments of the present disclosure may be not limited to the embodiments introduced and described in the present disclosure explicitly.

What is claimed is:

1. A membrane oxygenator with a built-in filter, comprising:
an upper cover, which is divided into a first blood path space, a first gas path space, and a first water path space in turn from a center to an outer edge, wherein the upper cover is provided with a gas inlet connected with the first gas path space, a first vent connected with the first blood path space, and a water inlet connected with the first water path space;
a lower cover, which is divided into a second blood path space, a second gas path space, and a second water path space in turn from a center to an outer edge, wherein the lower cover is provided with a blood outlet connected with the second blood path space, a gas outlet connected with the second gas path space, and a water outlet connected with the second water path space;
a shell, wherein two ends of the shell are respectively connected with the upper cover and the lower cover, and a blood inlet connected with an inner cavity of the shell is arranged on the shell near the upper cover;
an oxygenation structure, which is disposed in the inner cavity of the shell, including a mandrel, a filter screen, an oxygen pressure membrane, and a temperature-changing membrane, wherein an upper end of the mandrel enters the first blood path space, the upper end of the mandrel is opposite to the first vent, a lower end of the mandrel is opposite to the blood outlet, the filter screen is a pleated filter screen, the filter screen is disposed around the mandrel, a gap is arranged between the filter screen and the mandrel, the oxygen pressure membrane is wrapped on an outer surface of the filter screen, the oxygen pressure membrane is connected with the first gas path space and the second gas path space, the temperature-changing membrane is wrapped on an outer surface of the oxygen pressure membrane, and the temperature-changing membrane is connected with the first water path space and the second water path space; and
a gap arranged between the temperature-changing membrane and an inner wall of the shell, wherein a width of the gap gradually decreases from the upper cover to the lower cover.

2. The membrane oxygenator with the built-in filter of claim 1, wherein the membrane oxygenator further includes a first plugging layer and a second plugging layer, the first plugging layer is disposed at a junction of the shell and the upper cover, and the second plugging layer is disposed at a junction of the shell and the lower cover; and
an upper end of the filter screen is connected to the first plugging layer, and a lower end of the filter screen is connected to the second plugging layer.

3. The membrane oxygenator with the built-in filter of claim 2, wherein the oxygen pressure membrane includes a plurality of ventilation pipes, and each ventilation pipe of the plurality of ventilation pipes is a hollow pipe with openings at both ends;
one end of each ventilation pipe penetrates into the first plugging layer and is connected with the first gas path space, and the other end of each ventilation pipe penetrates into the second plugging layer and is connected with the second gas path space;
the temperature-changing membrane includes a plurality of temperature-changing pipes, and each temperature-changing pipe of the plurality of temperature-changing pipes is a hollow pipe with openings at both ends; and
one end of each temperature-changing pipe penetrates into the first plugging layer and is connected with the first water path space, and another end of each temperature-changing pipe penetrates into the second plugging layer and is connected with the second water path space.

4. The membrane oxygenator with the built-in filter of claim 1, wherein the membrane oxygenator further includes a turbulence structure for guiding blood to flow transversely, and the turbulence structure is disposed between the shell and the temperature-changing membrane.

5. The membrane oxygenator with the built-in filter of claim 4, wherein the turbulence structure includes a plurality of protrusions protruding from the inner wall of the shell towards the temperature-changing membrane.

6. The membrane oxygenator with the built-in filter of claim 5, wherein the plurality of protrusions are distributed in a ladder shape, and a distance between the temperature-changing membrane and the protrusion close to the upper cover is larger than a distance between the temperature-changing membrane and the protrusion close to the lower cover.

7. The membrane oxygenator with the bunt-in filter of claim 1, wherein the upper cover is further provided with a recirculation port, and the recirculation port is connected with the first vent.

8. The membrane oxygenator with the built-in filter of claim 1, wherein the shell is provided with a second vent.

9. The membrane oxygenator with the built-in filter of claim 8, wherein the second vent is provided with a unidirectional breathable membrane, and the unidirectional breathable membrane is used to intercept liquid in the shell and allow bubbles in the liquid to exit from the shell.

10. The membrane oxygenator with the built-in filter of claim 1, wherein the shell is a cylindrical shell, and an inner diameter of the shell decreases gradually from the upper cover to the lower cover; and
a cross section of the mandrel gradually decreases from the upper cover to the lower cover.

11. The membrane oxygenator with the built-in filter of claim 1, wherein the upper cover is provided with a first partition ring and a second partition ring, the second partition ring is disposed around the first partition ring, the first partition ring partitions the first blood path space and the first gas path space, and the second partition ring partitions the first gas path space and the first water path space; and
the lower cover is provided with a third partition ring and a fourth partition ring, the fourth partition ring is disposed around the third partition ring, the third partition ring partitions the second blood path space and the second gas path space, and the fourth partition ring partitions the second gas path space and the second water path space.

* * * * *